United States Patent [19]  
Harnden

[11] 3,931,397  
[45] Jan. 6, 1976

[54] BIOLOGICALLY ACTIVE MATERIAL
[75] Inventor: Michael Raymond Harnden, Horsham, England
[73] Assignee: Beecham Group Limited, England
[22] Filed: Nov. 8, 1973
[21] Appl. No.: 413,863

Related U.S. Application Data
[62] Division of Ser. No. 303,955, Nov. 6, 1972, Pat. No. 3,845,033.

[30] Foreign Application Priority Data
Nov. 5, 1971 United Kingdom............... 51514/71

[52] U.S. Cl. ................................................. 424/85
[51] Int. Cl.² ...................................... A61K 45/04
[58] Field of Search ..................................... 424/85

[56] References Cited
UNITED STATES PATENTS
3,679,654  7/1972  Macs........................... 260/211.5 R
3,725,545  4/1973  Macs................................. 424/180

Primary Examiner—Shep K. Rose

[57] ABSTRACT
This invention relates to antiviral substances, to a method for their preparation, and to pharmaceutical compositions comprising them.

5 Claims, No Drawings

BIOLOGICALLY ACTIVE MATERIAL

This is a division of application Ser No. 303,955 filed Nov. 6, 1972 which issued as U.S. Pat. No. 3,845,033 on Oct. 29, 1974. It is now generally recognised that double-stranded ribonucleic acids are potent inducers of interferons and thus should be of value in the broad spectrum prophylaxis of viral infections, and, to a lesser extent, in the treatment of such infections. Double-stranded ribonucleic acids of both natural and synthetic origin have been shown to possess interferon-inducing and antiviral activity in tissue-culture and in whole animals. Among the specific sources of interferon-inducing double-stranded ribonucleic acid which have been reported are the virus particles found in some strains of Penicillium chrysogenum, P.funiculosum, P.stoloniferum, Aspergillus niger and A.foetidus; cytoplasmic polyhedrosis virus; reovirus 3 virion; and the replicative form of MS2 coliphage and of MU9 mutant coliphage.

However, there is some evidence which suggests that double-stranded ribonucleic acid of natural origin may be unacceptably toxic in mammals, and its medical and veterinary use may be limited. There is thus a need for an antiviral agent which is less toxic than double-stranded ribonucleic acid alone, and which has comparable or better antiviral activity.

Polybases such as spermine, spermidine, cadaverine, polylysine, protamine and diethylaminoethyl dextran have been used in the past to stabilise nucleic acids generally, (and some synthetic double-stranded ribonucleic acids in particular) against thermal denaturation and nuclease degradation. When it was discovered that synthetic double-stranded ribonucleic acids were inducers of interferon, many workers believed that treatment of the double-stranded ribonucleic acid with polybases such as these would result in stabilisation against degradation by ribonuclease, and thus in improved or prolonged in vivo antiviral activity. Most of the interferon-related biological work carried out in the past has involved the separate addition of the polybase to synthetic double-stranded ribonucleic acids, mainly Poly I:Poly C. However, the results of this work were not encouraging. Elevated interferon levels were obtained in tissue cultures (refs. 1,2,3,4,5 and 6 below) but where the activities of polybase-treated synthetic ribonucleic acids were examined in whole animals (refs. 1,6) neither protection against virus nor toxicity were substantially changed.

REFERENCES:
1. G. P. Lampson, A. A. Tytell, A. Kirk Field, M. M. Nemes, and M. R. Hilleman, Proc. Soc. Exptl. Biol. Med., 132, 1969, 212.
2. F. Dianzani, S. Baron, C. E. Buckler, and H. B. Levy, Proc. Soc. Exptl. Biol. Med., 136, 1971, 1111.
3. J. Y. Richmond, Arch. fur die gesamte Virusforschung, 33, 1971, 242.
4. J. G. Tilles, Proc. Soc. Exptl. Med., 133(4), 1970, 1334.
5. A. Billiau, C. E. Buckler F. Dianzani, C. Uhlendorf, and S. Baron, Ann. N.Y. Acad. Sci., 173(1), 1970, 657.
6. B. D. Rosenquist, Am.J.Vet.Res., 32(1), 1971, 35.

This invention is based on the discovery that polymeric polycations having a plurality of quaternary nitrogen sites form strong complexes with natural double-stranded ribonucleic acids, which complexes have good antiviral activity, at least in small mammals.

It should perhaps be noted that Gabbay et.al. (Ann. N.Y. Acad. Sci., 171(3), 1970, 810; and Biochemistry, 10(9), 1971, 1665) have studied the interaction of some monomeric quaternary ammonium compounds with (inter alia) the double-stranded synthetic ribonucleic acid Poly A:Poly U. However, their reports concern only the physico-chemical properties and structure of the complexes, and in addition, they have not reported work with polyquaternary ammonium compounds. Also, British Pat. No. 1,230,065, refers to the use of cetyltrimethylammonium bromide as a precipitating agent for double-stranded ribonucleic acid of natural origin. We have, however, tested the complex of cetyltrimethylammonium bromide with a natural double-stranded ribonucleic acid, and find no significant difference between the toxicity and antiviral activity of the complex, and that of the double-stranded ribonucleic acid itself.

According to the present invention there is provided an antiviral substance which is a principally ionic complex in which the cations are organic polymer polycations which have a plurality of quaternary nitrogen sites located at intervals along the polymer chains and the anions are either (a) double-stranded ribonucleic acid polyanions, said double-stranded ribonucleic acid being of natural origin or (b) polyanions of a double-stranded derivative of a double-stranded ribonucleic acid of natural origin.

The term "double-stranded" used in connection with ribonucleic acid refers to the characteristic whereby two ribonucleic acid molecules are associated by hydrogen bonding between complementary bases in each molecule. Ribonucleic acids may vary in the degrees of "double-strandedness".

The term "double-stranded ribonucleic acid of natural origin" means any double-stranded ribonucleic acid which is isolatable from a naturally-occurring source (e.g. those sources listed earlier in this specification), and excludes synthetic double-stranded ribonucleic acids such as Poly I:Poly C, Poly A:Poly U and Poly G:Poly C.

The term "double-stranded derivative of a double-stranded ribonucleic acid of natural origin" means any double-stranded ribonucleic acid of natural origin which has been subjected to a chemical or biochemical (e.g. enzymatic) reaction which alters the primary and/or secondary and/or tertiary structure (e.g. the N-oxides described in our British patent application No. 19448/70 which corresponds to my German Offenlegungsschrift No. 2,122,644, Nov. 25, 1971 and chem. Abstracts 76, 59983v (1972), or the alkali-modified double-stranded ribonucleic acids described in our British patent application No. 1940/71) which corresponds to Harnden and Sharp (commonly assigned) German Offenlegungsschrift No. 2,202,513 July 27, 1972 and chem Abstracts 78, 4166k (1973), provided that the resultant derivative retains a substantial degree of base-pairing between complementary strands.

The double-strandedness of a double-stranded ribonucleic acid or a derivative of a double-stranded ribonucleic acid can be measured by two parameters known as the hyperchromicity and Tm. These parameters are obtained by recording the ultra violet absorption of the material at $258\mu$ while gradually raising the temperature of the material. The u.v. absorption value of a double-stranded material at this frequency increases with increasing temperature until a constant value is reached, corresponding to the absorption of the thermally denatured (i.e. single-stranded) ribonucleic acid. The difference between the two extremes of absorption expressed as a percentage of the absorption of the double-stranded material is termed the "hyperchromicity" of that material.

When the u.v. absorption at 258µ of a double-stranded material is plotted against temperature, it is found that the absorption is greater at high than at low temperatures. The temperature at which the absorption is mid-way between the absorption of the double-stranded stranded material and that of the thermally denatured (i.e. single-stranded) material is called the Tm of the material.

The cationic moiety present in the complexes of this invention has been defined as an organic polymer cation which has a plurality of quaternary nitrogen sites located at intervals along the polymer chain. One group of suitable organic polymer polycations is the group of structure (I):-

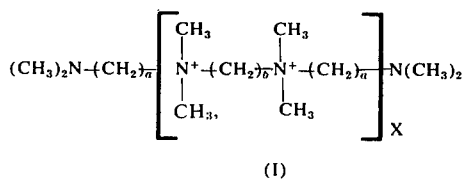

(I)

wherein a and b are integers which are the same or different and each is from 2 to 10; X is an integer or fractional number ≥ 2 which depends on the length of the polymer chain.

Another group of suitable polycations is the group of formula(I) wherein the carbon chain between quaternary nitrogen sites contains olefinic or acetylenic bonds, or carries methyl substituents.

The polyanions present in the complex of this invention are (a) double-stranded ribonucleic acid polyanions, said double-stranded ribonucleic acid being of natural origin or (b) polyanions of a double-stranded derivative of a double-stranded ribonucleic acid of natural origin. Preferred sources of double-stranded ribonucleic acid include the virus-like particles found in certain of the Penicillia, e.g. *P.chrysogenum* (British Pat. No. 1,170,929), *P.stoloniferum* (Banks et al.Nature 218,542 (1968), *P.cyanoofulvum* (Banks et al.Nature 223, 155 (1968)), and in certain of the Aspergilli e.g. *A.niger* and *A.foetidus* (our copending patent application No. 13826/70) which corresponds to U.S. Ser. No. 124,496 filed Mar. 15, 1971, abandoned in favor of continuation application Ser. No.282,365, filed Aug. 22, 1972, abandoned in favor of continuation application Ser. No. 487,279, filed July 10, 1974, of Chain et al. Preferably also the component (a) or (b) should be capable of inducing interferon production in live mammals. (This can be confirmed by the method of Lampson et al. G. P. Lampson, A. A. Tytell, A. K. Field, M. M. Nemes and M. R. Hillerman *Proc.Nat.Acad.Sci.*,58 (1967),782).

The antiviral substance of this invention has been described as a principally ionic complex. The complex is characterised by a strong electrostatic interaction between the polymeric cationic moiety and the ribonucleic acid anionic moiety. However, other types of interaction may well operate. For example, it is believed that some form of "hydrophobic" bonding exists between the two components, although the precise nature of such bonding is not yet understood.

The preferred complexes of this invention are those in which all or almost all of the anionic sites on the double-stranded ribonucleic acid anions are neutralised by the quaternary cationic sites on the quaternary polymer. Such complexes may be termed "1:1 complexes" or "highly neutralised complexes".

The complexes of this invention may be prepared by a process which comprises contacting, in solution, organic polymer cations which have a plurality of quaternary nitrogen sites located at intervals along the polymer chains with either (a) double-stranded ribonucleic acid polyanions, said double-stranded ribonucleic acid being of natural origin or (b) polyanions of a double-stranded derivative of a double-stranded ribonucleic acid of natural origin.

Although all of the complexes of this invention can be made by the above-defined process, the physical characteristics of the complexes depend to some extent on the detailed method by which the polycations and polyanions are brought into contact. For the purposes of explanation the complexes of this invention can conveniently be divided into two arbitrary classes, namely those which are soluble in 0.15M Na Cl solution (hereafter referred to as "soluble complexes" and those which are insoluble in 0.15M Na Cl (hereafter referred to as "insoluble complexes").

In general, we have observed "insoluble complexes" are prepared by slowly adding a solution of the polyquaternary component to a dilute solution of the double-stranded ribonucleic acid component (e.g. about 0.5 mg/ml.) For example, a solution or an organic polymer containing the desired polycation can be made up in aqueous solution of an inorganic salt, e.g. Na Cl. A similar solution of the ribonucleic acid component can be made up in an aqueous solution containing an inorganic salt. The polyquaternary solution may then be added to the ribonucleic acid solution with stirring and, providing the molarity of the resultant salt solution is not too high, the desired complex will precipitate directly. If it does not precipitate, the solution can be diluted to reduce the molarity below the critical level and the desired complex will then precipitate. Alternatively, a physical mixture of a neutral polymer containing the polycation and the ribonucleic acid or ribonucleic acid derivative can be added to a salt solution, and if necessary, the resultant solution can be diluted to precipitate the desired complex. Preferably, in both of the above methods of preparing "insoluble complexes", a molar excess of the organic polymer polycation is contacted with the ribonucleic acid polyanion (the molar excess being calculated on the basis of the number of basic sites capable of reacting with the phosphoric acid sites on the ribonucleic acid polyanions).

It will be realised from the above paragraph that it is relatively easy to produce the "insoluble complexes" of this invention. More care, however, is required to produce the "soluble complexes".

To produce the soluble complexes a solution of the polyquaternary compound is added slowly, with stirring, to a solution of the double-stranded ribonucleic acid or ribonucleic acid derivative in aqueous Na Cl, 0.15M, until just before precipitation begins or until only a small amount of precipitation takes place. Any precipitate is then removed, leaving the desired complex in solution. In general, extensive precipitation should be avoided, since homogeneity of the complex left in solution cannot be guaranteed if much precipitation is allowed to take place. We prefer to add the solution of polyquaternary compound to a solution of the double-stranded ribonucleic acid or ribonucleic acid derivative containing not less than about 5 mg/ml (e.g. 5 – 20 mg/ml) since at higher dilutions it appears that almost all the ribonucleic acid is precipitated as insoluble complex.

As has already been indicated, the preferred complexes of this invention are those having a high degree e.g. more than 60%, preferably more than 75%) of charge neutralisation. Also, because they are more conveniently administered and in some cases possess advantageous biological properties relative to the "insoluble complexes", those complexes which are soluble in isotonic saline are preferred. However, "soluble complexes" cannot conveniently be prepared using all polyquaternary compounds, since with some, precipitation of an "insoluble complex" occurs before sufficient polyquaternary compound has been added to achieve a high degree of charge neutralisation. While it must ultimately be a matter of trial and error to test whether a "soluble complex" can be made with any particular polyquaternary compound, certain guidelines can be laid down. Thus, we have noted that when polyquaternary compounds of structure (I) are employed there is a direct relationship between the equivalent weight of the polyquaternary compound and the degree of neutralisation obtainable with that polyquaternary compound before precipitation of "insoluble complex" begins. (The equivalent weight is the molecular weight of the polycation divided by the number of basic nitrogen sites per molecule). We have noted that with quaternary polycations of structure (I) having a low equivalent weight more polycation can be complexed with the ribonucleic acid before precipitation of "insoluble complex" begins than with quaternary polycations of structure (I) having a higher equivalent weight. This tendency will be illustrated in the Specific Examples later in this specification.

It is perhaps worthwhile emphasising again that when we speak of "insoluble complexes" in this invention, we mean complexes which are insoluble in 0.15M NaCl solution. In face most, if not all, of these "insoluble complexes" can be dissolved in concentrated electrolyte solutions, but in such concentrated electrolyte, the complexes are dissociated. This is in contrast with the "soluble complexes" which, when in solution in 0.15M NaCl, are believed to be substantially non-dissociated.

The complexes of this invention (both "soluble" and "insoluble") are antiviral in activity, having a wide spectrum of activity against a variety of DNA and RNA viruses, e.g. encepholomyocarditis (EMC) virus, Semliki Forest virus, Foot and Mouth disease virus and Herpes Simplex virus. It is believed that their mode of action is principally by induction of interferon in host cells, thereby conferring protection against virus attack. For this reason it is believed their primary utility lies in the prophylaxis of virus infection rather than in the treatment of established infections. The complexes are in general more resistant to ribonuclease degradation than the double-stranded ribonucleic acid itself.

Thus, in another of its aspects, the present invention provides a pharmaceutical composition comprising an antiviral complex as defined hereinbefore and one or more pharmaceutically acceptable carriers.

The choice of pharmaceutical carrier is determined by the preferred mode of administration and standard pharmaceutical practice. The mode of administration may be by injection, e.g. subcutaneously, intravenously or intramuscularly, in which case the carrier will be an injectable liquid in which the complex may be dissolved, or suspended as a fine dispersion. However, even with the "soluble complexes" of this invention it may be difficult to redissolve them once they have been isolated (e.g. by freeze drying) and we therefore prefer to form the complex in situ in the injectable liquid (e.g. isotonic saline). For topical application the carrier may be a liquid for application to the mucous membrane. The composition of this invention may be administered alone or in combination with other agents used in the treatment of virus infections (e.g. vaccines) or for the relief of the symptoms of virus infections.

The following Examples are intended to illustrate the properties of, and methods of preparation of, some complexes of this invention, and also to illustrate in greater detail some of the features of the invention referred to earlier in this specification. In the following Examples, the abbreviation "d.s. RNA" stands for "double-stranded ribonucleic acid".

EXAMPLE I i. Preparation of Polyquaternary Ammonium Compounds as Starting Materials.

Table I lists the physical properties of a number of polyquaternary ammonium compounds which were synthesised as follows:

Compounds 1 – 7 were prepared by refluxing the appropriate N,N,N',N'-tetramethyldiamine (0.1 mole) and dibromoalkane (0.1 mole) in methanol (300 ml.) for 5 hours. The solution was cooled and concentrated at reduced pressure. The residue was dissolved in water (250 ml.) and the solution extracted with ethyl acetate (3 × 150 ml.). The aqueous solution was then concentrated at reduced pressure to half volume and dialysed against water (3 × 5 lit.). The solution inside the dialysis bag was then concentrated at reduced pressure and on trituration of the residue with ethanol (ca 100 ml.) a white solid was obtained.

For the preparation of compound 8, 0.09 mole of N,N,N',N'-tetramethyl-propane-1,3-diamine and 0.08 mole of 1,4-dibromobutane were used, and for the preparation of compound 9, 0.1 mole of N,N,N',N'-tetramethyl-butane-1,4,-diamine and 0.08 mole of 1,4-dibromobutane were used.

For the preparation of compound 10, 0.1 mole of N,N,N',N'-tetramethyl-propane-1,3-diamine and 0.08 mole of 1,4-dibromobutane were used and the dialysis stage was omitted. The residue obtained from concentration at reduced pressure of the ethyl acetate-extracted aqueous solution was triturated three times with boiling isopropanol (3 × 500 ml.), filtered and dried. The product was obtained as a fine white powder.

Compound 11 (hexadimethrine bromide) was purchased as "POLYBRENE" from Aldrich Chemical Company.

ii. Characterisation of Polyquaternary Ammonium Starting Materials

In their paper on the macromolecular properties of hexadimethrine bromide, Barlow and co-workers[2] suggest that reactions which could terminate the polymerisation are cyclisation and dehydrobromination.

[2] G. H. Barlow, L. J. Coen, E. T. Kimura and S. Keresztes-Nagy, Proc. Soc. Exp. Biol. Med., 113, 884 (1963).

The nmr spectra (determined in $D_2O$) of hexadimethrine bromide and the other saturated polyquaternary ammonium compounds synthesised in the present work provide no evidence for the presence of vinylic protons which would be present if chain termination occurred as result of dehydro bromination. There is, however, in each case a singlet at $\delta = 2.2-3$ p.m. which can be assigned to $-N(CH_3)_2$ protons. The nmr evidence therefore suggests that the polymer chains terminate in dimethylamine groups. Assuming this to be correct, it is possible to calculate an average molecular weight for the polymers from the ratio of the intensities of the resonances assigned to $-^+N(CH_3)_2$ protons (chain propagation) and those assigned to $-N(CH_3)_2$ protons (chain termination). Unfortunately the bands cannot be integrated with accuracy because of overlap of other resonances, but since the bands are both sharp singlets, the relative peak heights are taken as a first approximation.

e.g. For hexadimethrine bromide Compound 11, a=6; b=3)

$$\text{Intensity } \frac{+N(CH_3)_2}{N(CH_3)_2} = \frac{20.0}{1.7} = 11.8 \; (=x)$$

Therefore there are 2 chain terminations per 23.6 propagations.

Therefore M.W. = $116 + (23.6 \times 187.1) + 44 = 4590$.

This value is in reasonable agreement with the values of 3,800 and 4,100 found by Barlow and co-workers[2] for a standard batch of hexadimethrine bromide using sedimentation equilibrium and sedimentation velocity measurements.

In Table 1 structural and analytical data obtained for the polyquaternary compounds is summarised. Most of the polymers are extremely hygroscopic and as a consequence accurate elemental analyses are difficult to obtain.

EXAMPLE 2

Preparation of an isotonic saline insoluble complex from d.s.RNA isolated from P.chrysogenum virus-like particles and Hexadimethrine Bromide To a stirred solution of the ds.RNA (100 mg.) obtained from the virus particles found in *P.chrysogenum* ATCC 10002 in 0.15M sodium chloride (200 ml.) at room temperature was added a solution of hexadimethrine bromide (200 mg.) in 0.15M sodium chloride (200 ml.). A precipitate was obtained. The reaction mixture was stirred for 16 hr. at room temperature and then centrifuged. Measurement of the u.v. spectrum of the supernatant solution indicated that it contained no nucleic acid. The precipitate was washed with water (200 ml.) and then with methanol (200 ml.) and dried at room temperature in vacuo giving the product as a pellet (141 mg.).

PROPERTIES AND CHARACTERISATION OF THE COMPLEX

1. The product is soluble in 0.6M NaCl and higher molarities.
2. Ultraviolet spectral determinations with weighed quantities of the complex indicated that it contained $68 \pm 10\%$ nucleic acid. A neutral complex (1 $N^+$ per phosphate) would contain 76% nucleic acid. The product is probably the 1:1 neutral complex, but incomplete drying as a consequence of tightly bound solvent may have resulted in a low nucleic acid assay.
3. In solution in high molarity sodium chloride the complex appears to be dissociated. Addition of an equal volume of ethanol to a solution of the complex in 1.5M sodium chloride resulted in quantitative precipitation of the ds.RNA. The nucleic acid thus obtained had identical physical characteristics (hyperchromicity, $T_m$, gel electrophoresis pattern) to those of the original ds.RNA. Moreover, gel permeation chromatography of a solution of the complex in 1.5M NaCl on a Bio Gel [R] 150M column gave an identical u.v. trace to that of the original ds.RNA.

Table 1.

Polyquaternary Ammonium Compounds $$(CH_3)_2N-(CH_2)_{\overline{a}}\left[\begin{array}{c} CH_{3+} \; Br^- \; CH_{3+} \; Br^- \\ | \quad\quad\quad\quad | \\ N-(CH_2)_{\overline{b}}-N-(CH_2)_{\overline{a}} \\ | \quad\quad\quad\quad | \\ CH_3 \quad\quad\quad CH_3 \end{array}\right]_x -N(CH_3)_2$$

| Compound | a | b | Yield % | Calculated % C | H | N | Br | Found % C | H | N | Br | $-N(CH_3)_2-^+$ δ (ppm) | Peak Ht. | $-N(CH_3)_2$ δ (ppm) | Peak Ht. | Total No. Quaternary Sites (2x) | M.W. | Equiv. weight (m.w.) (2x+2) |
|---|---|---|---|---|---|---|---|---|---|---|---|---|---|---|---|---|---|---|
| 1 | 3 | 3 | 12.7 | 38.0 | 7.7 | 9.3 | 45.0 | 36.9 | 7.5 | 8.7 | 44.1 | 3.32 | 22.6 | 2.28 | 3.95 | 11.4 | 2020 | 151 |
| 2 | 2 | 4 | 18.1 | 36.5 | 7.4 | 8.7 | 47.4 | 35.4 | 7.4 | 8.3 | 46.6 | 3.36 | 24.8 | 2.95 | 1.0 | 49.6 | 8350 | 162 |
| 3 | 3 | 4 | 85.5 | 38.5 | 7.7 | 8.3 | 45.5 | 37.7 | 7.9 | 7.9 | 43.6 | 3.23 | 20.95 | 2.97 | 0.8 | 52.4 | 9200 | 169 |
| 4 | See footnote[a] | 3 | 31.1 | 39.8 | 7.3 | 8.7 | 44.3 | 37.0 | 7.3 | 7.6 | 42.2 | 3.26 | 22.4 | 2.30 | 2.7 | 17.1 | 3070 | 161 |
| 5 | 4 | 4 | 9.5 | 40.7 | 8.0 | 8.1 | 44.2 | 40.4 | 8.0 | 7.8 | 42.0 | 3.09 | 16.7 | 2.47 | 1.1 | 30.4 | 5620 | 173.5 |
| 6 | 6 | 4 | 41.2 | 44.1 | 8.5 | 7.4 | 40.0 | 42.9 | 8.4 | 7.0 | 39.0 | 3.12 | 24.6 | 2.99 | 1.0 | 49.2 | 9720 | 190 |
| 7 | 6 | 6 | 50.5 | 46.8 | 8.9 | 7.0 | 37.3 | 45.7 | 8.8 | 6.5 | 36.2 | 3.10 | 24.3 | 2.89 | 1.7 | 28.6 | 6130 | 200 |
| 8 | 3 | 4 | 33.1 | 39.8 | 8.0 | 8.9 | 43.3 | 38.8 | 7.9 | 8.0 | 42.3 | 3.23 | 23.0 | 2.30 | 4.05 | 11.4 | 2100 | 157 |
| 9 | 4 | 4 | 20.2 | 41.3 | 8.2 | 8.4 | 42.2 | 40.3 | 8.1 | 8.1 | 42.8 | 3.17 | 25.0 | 2.62 | 3.2 | 15.6 | 2950 | 168 |
| 10 | 3 | 4 | 51.3 | 40.5 | 8.1 | 9.3 | 42.1 | 37.7 | 8.0 | 8.3 | 43.3 | 3.23 | 24.6 | 2.48 | 6.3 | 7.8 | 1480 | 151 |
| 11 | 6 | 3 | — | 42.8 | 8.3 | 7.8 | 41.1 | 41.3 | 8.5 | 7.4 | 40.7 | 3.19 | 20.0 | 2.75 | 1.7 | 23.6 | 4590 | 171 |

[a] $-CH_2-CH=CH-CH_2-$

4. Reduction of the molarity of a solution of the complex to below 0.6M in sodium chloride results in precipitation of the complex.

pared in 16–20 g. mice of the strain CD1. The compounds were administered by intraperitoneal injection, and the animals observed for 10 days after.

Table 3

| Compound | Dose[a] (mg/kg) | Mortality | Time of occurrence of deaths | LD$_{50}$ (mg/kg) |
|---|---|---|---|---|
| ds-RNA[b] -hexadimethrine complex | 10 | 0/10 | | |
|  | 20 | 0/10 | | |
|  | 40 | 0/10 | | >160 |
|  | 80 | 0/10 | | |
|  | 160 | 1/10 | 10 days after administration | |
| ds-RNA[c] | 10 | 0/10 | | |
|  | 20 | 3/10 | 12–72 hours after administration | 35 |
|  | 40 | 9/10 | | |
|  | 80 | 6/10 | | |

[a]Dose refers to ds-RNA present in each case
[b]Administered as a solution in 1.5M NaCl
[c]Administered as a solution in 0.15M NaCl

ANTIVIRAL ACTIVITY OF THE COMPLEX

An intraperitoneal injection of the test compound was administered to 16–20 g. mice of the strain CD1. Either 24 hours or 72 hours later these mice were challenged with varying dilutions of encephalomyocarditis (EMC) virus also administered by the intraperitoneal route. The animals were observed for 12 days and the mortality ratios and the mean survival times of treated mice were compared with those of untreated control mice. The mean survival time was calculated as follows:

$$S.T. = \frac{N}{\frac{n}{x}}$$

where $N$ = number of animals in a group
$n$ = number of animals on day $x$

EXAMPLE 3

Preparation of isotonic saline-insoluble complexes from d.s RNA isolated from P.chrysogenum virus — like particles and polyquaternary compounds 3,5 and 10.

The procedure described in Example 2 for the preparation the isotonic saline-insoluble complex of hexadimethrine bromide and d.s RNA was followed exactly using polyquaternary compounds 3, 5 and 10 described in Example 1. The resultant complexes were designated $C_a$, $C_b$ and $C_c$ respectively. Complex $C_a$ was only soluble in aqueous Na Cl at ionic concentrations higher than 1.5N; complex $C_b$ was soluble in aqueous saline at ionic concentrations greater than 0.6M; while complex $C_c$ was soluble in aqueous Na Cl at ionic concentrations greater than 0.45M. Thus, there appears to be a rela-

| Compound | Time between drug and subsequent virus (hours) | Dose[a] (μg/mouse) | Virus Challenge 10$^{-4}$ Mortality | Survival Time | Virus Challenge 10$^{-5}$ Mortality | Survival Time |
|---|---|---|---|---|---|---|
| ds-RNA[b] -hexadimethrine complex | 72 | 1 | 8/10 | 6.0 | 8/10 | 6.7 |
|  |  | 10 | 7/10 | 7.0 | 1/10 | 50.0 |
|  |  | 100 | 0/10 | 00 | 0/10 | 00 |
|  | 24 | 1 | 8/10 | 7.8 | 3/10 | 20.4 |
|  |  | 10 | 4/10 | 26.7 | 1/10 | 90.1 |
|  |  | 100 | 2/10 | 39.7 | 0/10 | 00 |
| ds-RNA[c] | 72 | 1 | 10/10 | 4.7 | 8/10 | 5.9 |
|  |  | 10 | 7/10 | 6.9 | 6/10 | 11.6 |
|  |  | 100 | 7/10 | 8.8 | 1/10 | 50.0 |
|  | 24 | 1 | 7/10 | 8.2 | 5/10 | 12.9 |
|  |  | 10 | 4/10 | 14.9 | 2/10 | 25.0 |
|  |  | 100 | 1/10 | 40.0 | 2/10 | 29.4 |
| Untreated |  |  | 19/20 |  | 18/20 |  |

[a]Dose refers to amount of ds-RNA present in each case
[b]Administered as a solution in 1.5M NaCl
[c]Administered as a solution in 0.15M NaCl

TOXICITY OF THE COMPLEX

The toxicity of the ds-RNA starting material and that of the hexadimethrine-ds-RNA complex were comtionship between the molecular weight of the polyquaternary compoound and the ionic concentration required for dissociation of its complex with d.s RNA.

The antiviral activity and toxicity of complexes $C_a$, $C_b$ and $C_c$ were tested as in Example 2. The results are summarised in Table 4.

Table 4

Antiviral Activity and Toxicity of Insoluble dsRNA-Polyquaternary Ammonium Complexes
No. Dead/Total No. in Group

ANTIVIRAL DATA (EMC)

| Complex No. | Compound administered 3 days prior to virus infection | | | | | | | | | | | |
|---|---|---|---|---|---|---|---|---|---|---|---|---|
| | Virus Dose $10^{-4}$ | | | Virus Dose $10^{-5}$ | | | Virus Dose $10^{-4}$ | | | Virus Dose $10^{-5}$ | | |
| | \multicolumn{12}{c}{Compound Dose (mg/kg)$^a$} | | | | | | | | | | |
| | 5 | 0.5 | 0.05 | 5 | 0.5 | 0.05 | 5 | 0.5 | 0.05 | 5 | 0.5 | 0.05 |
| $C_a$ d.s RNA | 0/10 | 2/10 | 9/10 | 1/10 | 3/10 | 6/10 | 0/10 | 1/10 | 4/10 | 0/10 | 1/10 | 1/10 |
| alone | 7/10 | 7/10 | 8/10 | 0/9 | 4/10 | 8/10 | 1/10 | 1/10 | 9/10 | 0/10 | 0/10 | 3/10 |
| $C_b$ d.s RNA | 1/10 | 9/10 | 10/10 | 2/10 | 4/10 | 10/10 | 0/9 | 7/9 | 9/10 | 0/10 | 3/10 | 8/10 |
| alone | 9/10 | 8/10 | 9/10 | 6/10 | 6/9 | 10/10 | 0/10 | 4/10 | 8/10 | 2/10 | 2/10 | 9/10 |
| $C_c$ d.s RNA | 3/10 | 8/10 | 10/10 | 0/10 | 4/10 | 8/10 | 0/10 | 2/10 | 1/10 | 0/10 | 1/10 | 0/10 |
| alone | 9/10 | 10/10 | 10/10 | 4/10 | 5/10 | 10/10 | 2/10 | 5/10 | 9/10 | 0/10 | 4/10 | 6/10 |

TOXICITY (I.P.)

| Complex No. | Compound Dose (mg/kg)$^a$ | | | | | | | | $LD_{50}$ (mg/kg) |
|---|---|---|---|---|---|---|---|---|---|
| | 200 | 160 | 100 | 80 | 50 | 40 | 25 | 20 | |
| $C_a$ d.s RNA | | 1/10 | | 0/10 | | 0/10 | | 0/10 | 160 |
| alone | | | | 9/10 | | 4/10 | | 0/10 | 45 |
| $C_b$ d.s RNA | 0/10 | | 0/10 | | 0/10 | | 0/10 | | 200 |
| alone | 10/10 | | 5/5 | | 10/10 | | 2/10 | | 30 |
| $C_c$ d.s RNA | 4/6 | | 10/10 | | 7/10 | | 2/10 | | 41$^b$ |
| alone | 10/10 | | 9/10 | | 10/10 | | 10/10 | | 25 |

$^a$Dose refers to amount of d.s RNA present in each case. d.s RNA administered as a solution in 0.15M Na Cl and complexes as a solution in 1.5M Na Cl.
$^b$At every dose level deaths occurred 2 days later than with dsRNA alone.

EXAMPLE 4

Preparation of isotonic saline-soluble complexes of polyquaternary compounds and d.s RNA isolated from the virus-like particles found in P.chrysogenum Complexing procedure To a viscous solution of d.s RNA (5-20 mg/ml.) obtained from the virus particles found in *P.chrysogenum* ATCC 1002 in 0.15M NaCl, a solution of the polyquaternary ammonium compound in 0.15M NaCl is added in small portions with constant agitation. The amount of the polyquaternary compound which can be added in this manner before precipitation occurs varies with the structure of the polyquaternary compound (see Table 5). e.g. Preparation of Complex $C_1$.

To a solution of d.s RNA (154 mg.) in 0.15M NaCl (10 ml.) a solution of the polyquaternary ammonium compound 1 ($a = b = 3$, $x = 5.7$; 67.5 mg.) in 0.15M NaCl (5.4 ml.) is added in small portions with constant agitation. A clear solution is obtained which can be diluted with 0.15M sodium chloride to any desired concentration.

Table 5

Polyquaternary Ammonium Compound-Double Stranded RNA Complexes
A solution of the appropriate polyquaternary ammonium compound in 0.15M sodium chloride (5.4 ml.) was added in small portions, with constant agitation, to a solution of double stranded RNA (154 mg.) in 0.15M sodium chloride (10 ml.).

| Complex No. | Polyquaternary Ammonium$^a$ Compound Structure ($a/b^{2x}$) | Weight polyquaternary ammonium compound added without precipitation (mg) | % phosphate$^b$ charge neutralisation | Electrophoretic Mobility$^c$ of dsRNA |
|---|---|---|---|---|
| C1 | $3/3^{11.4}$ | 67.5 | 100 | 0.53 |
| C2 | $2/4^{49.6}$ | 57.9 | 80 | 0.62 |
| C3 | $3/4^{52.4}$ | 60.5 | 80 | 0.62 |
| C4 | butene/$3^{17.1}$ | 57.4 | 80 | 0.66 |
| C5 | $4/4^{30.4}$ | 46.5 | 60 | d |
| C6 | $6/4^{49.2}$ | 33.9 | 40 | 0.75 |
| C7 | $6/6^{28.6}$ | 35.8 | 40 | 0.79 |
| C8 | $3/4^{11.4}$ | 70.1 | 100 | 0.58 |
| C9 | $4/4^{15.6}$ | 60.0 | 80 | 0.56 |
| C10 | $3/4^{\ 7.8}$ | 67.5 | 100 | 0.56 |
| C11 | $6/3^{23.6}$ | 45.9 | 60 | 0.73 |

$^a$See Table 1.
$^b$Based on equivalent weights from Table 1 and average m.w. dsRNA nucleotide = 344.5
$^c$ For electrophoresis 4% polyacrylamide gels containing 0.04% bis acrylamide were prepared in glass tubes, 4 mm internal diameter. Running buffer was tris (0.04M), sodium acetate (0.2M), EDTA (0.002M), pH 7.8. Electrophoresis was carried out at 5mA/tube for 2 hr. DsRNA is separated into 3 bands with only slightly different mobilities. The relative mobility values for the complexes are based upon the median mobility of the 3 bands.
$^d$Did not move onto gel.

Physico-chemical Properties of Complexes

1. When dilute solutions of the complexes in 0.15M sodium chloride are heated to about 50°, precipitation occurs.

2. Electrophoresis

4% polyacrylamide gels containing 0.04% bisacrylamide were prepared in glass tubes, 4 mm internal diameter. Running buffer was tris (0.04M), sodium acetate (0.02M), EDTA (0.002M), pH 7.8. Electrophoresis was carried out at 5 mA/tube for 1–3 hr.

The complexes generally moved as discreet single bands with a lower mobility than dsRNA. Within the series, the electrophoretic mobility of the complexes decreases with increasing neutralisation of the nucleic acid phosphate charge (Table 5). Complex C5 gave a highly aggregated gel rather than a viscous solution, and on electrophoresis did not move on to the polyacrylamide gel.

3. Degradation by Ribonucleases of Human Serum

Three representative complexes were tested for their relative susceptibility to dilute human serum.

The incubation conditions were:
0.1 ml 0.06M tris-HCl buffer pH 7.6, in 0.6M NaCl
0.1 ml nucleic acid complex 1 mg/ml in 0.15M NaCl
0.1 ml human serum diluted with water 1 in 5 to 1 in 100.

The mixture was incubated for 30 min at 37°C, after which 0.1 ml was removed, mixed with 0.1 ml buffer D (0.05M NaCl, 0.001M EDTA, 20% sucrose, pH 7) and 50–100 μl subjected to electrophoresis for 3–4 hours, (electrophoresis conditions as in 2 above).

The gels were scanned using an ultraviolet spectrometer equipped with a linear transport scanner, and the peaks integrated.

| Serum Dilution | % Degradation of Nucleic Acid[a] | | | |
|---|---|---|---|---|
| | C1 | C3 | C10 | dsRNA |
| 1/100 | 3 | 0 | 3 | 35 |
| 1/50 | 7 | 0 | 13 | 100 |
| 1/10 | | 0 | 11 | 100 |
| 1/5 | | 0 | 11 | 100 |

[a]Based on disappearance of original nucleic acid band

Thus complexes C1 and C are considerably more resistant to human serum ribonucleases than is dsRNA itself, and C3 is completely resistant.

BIOLOGICAL PROPERTIES OF COMPLEXES

1. Toxicity

Acute intraperitoneal toxicities were determined in mice (Table 6). The complexes were generally slightly more toxic than dsRNA. The minimum lethal dose for dsRNA is about 20 mg/kg, whereas for many of the complexes it is 10–12.5 mg/kg. The highly aggregated C5 was considerably less toxic, however, and the complexes C6 and C7 prepared from the more hydrophobic polyquaternary ammonium compounds and in which there was less neutralisation of the phosphate charge, were also slightly less toxic than dsRNA.

2. Antiviral Activity

The protection afforded by the complexes against mouse EMC virus is summarised in Table 7 and Table 7A gives the results found with untreated controls.

Complexes C1, C2, C3, C4, C9, C10 and C11 have better antiviral activity than dsRNA when given 3 days before virus infection, and as good or better when given 1 day before infection.

Table 6

Toxicity of Complexes
The acute toxicity was determined for mice, strain CD1, weighing 18–22 g.
The animals were observed for 7 days after dosing by the intraperitoneal route and deaths recorded.

| Complex No. | No. Dead/Total No. in Group at Stated Dose (mg/Kg)[a] | | | | | | | | | | | Approximate $LD_{50}$ (mg/Kg) |
|---|---|---|---|---|---|---|---|---|---|---|---|---|
| | 200 | 100 | 80 | 50 | 40 | 25 | 20 | 12.5 | 10 | 5 | 2.5 | |
| C1 | | | | 10/10 | | 6/10 | | 4/10 | | | | 17.5 |
| C2 | | 5/6 | | 7/10 | | 4/10 | | 2/10 | | 31 | | |
| C3 | | | 10/10 | | 9/10 | | 4/10 | | 3/10 | 22 | | |
| C4 | | 5/5 | | 10/10 | | 9/10 | | 9/10 | | <12.5 | | |
| C5 | 10/10 | 2/10 | | 0/10 | | 0/10 | | 0/10 | | 115 | | |
| C6 | | 7/7 | | 7/10 | | 0/10 | | 0/10 | | 45 | | |
| C7 | | | | 3/10 | | 0/10 | | 0/10 | | >50 | | |
| C8 | | | | 10/10 | | 10/10 | | 5/10 | | 12.5 | | |
| C9 | | 10/10 | | 6/10 | | 8/10 | | | | <25 | | |
| C10 | | 10/10 | | 9/10 | | 6/10 | | | | 21 | | |
| C11 | | 10/10 | | 10/10 | | | | | | <50 | | |

[a]The dose refers to the nucleic acid component in each case

Table 7

Antiviral Activity of Complexes
Mice, strain CD1, weighing 18–22 g., were administered compounds by the intraperitoneal route either 24 or 72 hours prior to infection with EMC virus, also by the intraperitoneal route. Deaths were recorded daily for 13 days.

| Experiment No. | Complex No. | Animals dosed 3 days prior to Virus infection | | | | | | Animals dosed 1 day prior to Virus infection | | | | | |
|---|---|---|---|---|---|---|---|---|---|---|---|---|---|
| | | Virus Dose $10^{-4}$ | | | Virus Dose $10^{-5}$ | | | Virus Dose $10^{-4}$ | | | Virus Dose $10^{-5}$ | | |
| | | 5 | 0.5 | 0.05 | 5 | 0.5 | 0.05 | 5 | 0.5 | 0.05 | 5 | 0.5 | 0.05 |
| 1 | C2 | 4/10 | 9/10 | 10/10 | 0/10 | 4/10 | 7/10 | 2/10 | 0/10 | 2/10 | 0/10 | 0/10 | 1/10 |
| | C3 | 3/10 | 6/10 | 9/10 | 2/10 | 5/10 | 6/10 | 0/10 | 0/10 | 7/10 | 0/10 | 0/10 | 2/10 |
| | C11 | 5/10 | 10/10 | 10/10 | 0/9 | 7/10 | 9/10 | 2/10 | 3/10 | 7/10 | 0/8 | 0/10 | 3/10 |
| | dsRNA | 8/10 | 10/10 | 10/10 | 5/10 | 5/10 | 8/10 | 1/10 | 1/10 | 5/9 | 0/10 | 1/10 | 3/10 |
| 2 | C4 | 0/10 | 8/10 | 8/10 | 1/10 | 2/10 | 7/10 | 0/9 | 1/10 | 2/10 | 0/10 | 4/10 | 1/10 |
| | C5 | 2/10 | 7/10 | 10/10 | 1/10 | 7/10 | 9/10 | 2/10 | 5/9 | 8/10 | 1/10 | 3/10 | 4/10 |
| | C6 | 3/10 | 8/10 | 10/10 | 1/9 | 7/10 | 8/10 | 0/10 | 4/10 | 5/10 | 0/10 | 0/9 | 3/10 |
| | dsRNA | 3/7 | 8/10 | 8/10 | 0/10 | 4/10 | 7/10 | 0/10 | 2/10 | 0/10 | 1/10 | 1/10 | 2/10 |

Table 7-continued

Antiviral Activity of Complexes
Mice, strain CD1, weighing 18–22 g., were administered compounds by the intraperitoneal route either 24 or 72 hours prior to infection with EMC virus, also by the intraperitoneal route.
Deaths were recorded daily for 13 days.

| Experiment No. | Complex No. | Animals dosed 3 days prior to Virus infection | | | | | | Animals dosed 1 day prior to Virus infection | | | | | |
|---|---|---|---|---|---|---|---|---|---|---|---|---|---|
| | | Virus Dose $10^{-4}$ | | | Virus Dose $10^{-5}$ | | | Virus Dose $10^{-4}$ | | | Virus Dose $10^{-5}$ | | |
| | | 5 | 0.5 | 0.05 | 5 | 0.5 | 0.05 | 5 | 0.5 | 0.05 | 5 | 0.5 | 0.05 |
| 3 | C10 | 1/10 | 7/10 | 9/10 | 1/10 | 7/10 | 9/10 | 2/9 | 2/10 | 5/10 | 0/10 | 1/10 | 3/10 |
| | dsRNA | 9/10 | 10/10 | 10/10 | 4/10 | 5/10 | 10/10 | 2/10 | 5/10 | 9/10 | 0/10 | 4/10 | 6/10 |
| | C1 | 5/10 | 8/10 | 10/10 | 4/10 | 1/10 | 7/10 | 0/10 | 0/10 | 6/10 | 1/10 | 1/10 | 0/10 |
| 4 | C7 | 5/10 | 8/10 | 10/10 | 1/10 | 4/10 | 5/10 | 2/10 | 4/10 | 9/10 | 0/10 | 1/10 | 1/10 |
| | C9 | 1/10 | 8/10 | 8/10 | 1/10 | 3/10 | 7/10 | 2/10 | 3/10 | 2/7 | 0/10 | 1/10 | 1/10 |
| | dsRNA | 5/10 | 10/10 | 10/10 | 5/10 | 6/10 | 4/10 | 2/10 | 4/10 | 5/10 | 0/10 | 0/10 | 1/10 |

*a* The dose refers to the nucleic acid component in each case

Table 7(A)

| Experiment No. | Untreated Controls: Virus Dose $10^{-4}$ | Virus Dose $10^{-5}$ |
|---|---|---|
| | No. Dead/Total No. in group | |
| 1 | 20/20 | 19/20 |
| 2 | 20/20 | 18/20 |
| 3 | 20/20 | 20/20 |
| 4 | 20/20 | 20/20 |

EXAMPLE 5 a. Further Polyquaternary Ammonium Salt (Compound 12)

Compound 12 was prepared from N,N,N',N'-tetramethylbutane-1,3diamine (0.1 mole) and 1.4-dibromobutane (0.1 mole). After dialysis and concentration under reduced pressure a residue was formed which was triturated with isopropanol as for compound 10.

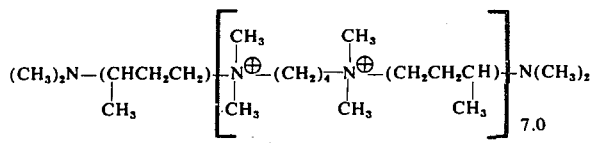

Compound 12 (an isomer)

Elemental Analysis: Calculated %: C, 41.5; H, 8.2; N, 8.4; Br, 42.0.
Found %: C, 40.8; H, 8.2; N, 7.4; Br, 41.1.

Nmr. data (D$_2$O): —N$^+$(CH$_3$)$_2$—, $\delta = 3.25$ ppm, peak Ht. 20.4; —N(CH$_3$)$_2$, $\delta = 2.45$ ppm, peak nt. 2.9. M.W. 2666. Equivalent Wt. 166.6.

b. Preparation of an isotonic saline insoluble complex from ds-RNA isolated from P. chrysegenum virus-like particles, and polyquaternary Compound 12

The procedure described in Example 2 was followed, using the polyquaternary compound described above. The complex, Complex C$_d$, was soluble in M sodium chloride solution.

The antiviral activity and toxicity of this insoluble complex is given in Table 8.

Table 8

Antiviral Activity and Toxicity of Ds-RNA and Insoluble and Soluble Ds-RNA - Polyquaternary Ammonium Complexes C$_d$ and C12
No. dead out of 10 in each group

| COMPOUND | ANTIVIRAL DATA (EMC) | | | | | | | | | | | | | TOXICITY (i.p.) | | | | |
|---|---|---|---|---|---|---|---|---|---|---|---|---|---|---|---|---|---|---|
| | Compound administered 3 days prior to virus infection | | | | | | Compound administered 1 day prior to virus infection | | | | | | | | | | | |
| | Virus Dose $10^{-4}$ | | | Virus Dose $10^{-5}$ | | | Virus Dose $10^{-4}$ | | | Virus Dose $10^{-5}$ | | | | | | | LD$_{50}$ |
| | 5 | 0.5 | 0.05 | 5 | 0.5 | 0.05 | 5 | 0.5 | 0.05 | 5 | 0.5 | 0.05 | 100 | 50 | 25 | 12.5 | (mg/kg) |
| ds-RNA | 7 | 9 | 10 | 3 | 6 | 10 | 0 | 4 | 9 | 0 | 2 | 1 | | 9 | 5 | 1 | 25 |
| Complex C12 | 3 | 6 | 10 | 1 | 2 | 4 | 1 | 1 | 4 | 0 | 0 | 0 | 10 | 10 | 10 | | <25 |
| Complex C$_d$ | 10 | 10 | 8 | 1 | 2 | 2 | 0 | 3 | 5 | 0 | 0 | 0 | 2 | 0 | 0 | | >100 |

| Untreated Controls Mortality | Virus Dose $10^{-4}$ 20/20 | Virus Dose $10^{-5}$ 19/20 |
|---|---|---| c. Preparation of an isotonic saline soluble complex from ds-RNA isolated from P. chrysogenum and polyquaternary compound 12

The soluble complex — Complex C12 — was prepared from ds-RNA (217 mg) in 0.15 M NaCl (10 ml) and a solution of polyquaternary compound 12 (84 mg) in 0.15 M NaCl (11.7 ml) in the manner described in Example 4. The complex has 80% charge neutralisation, and has a mobility 0.44 times the median mobility of ds-RNA.

The antiviral activity and toxicity of this complex are given in Table 8.

EXAMPLE 6 a. Preparation of an isotonic saline soluble complex from N-oxidised ds-RNA derived from P. chrysogenum The N-oxidised ds-RNA was prepared(using the procedure outlined in British Patent 1284150,), as follows:

Ds-RNA (300 mg) in 0.04 M potassium acetate, pH 8.2 (300 ml) was treated with a solution of m-chloroperbenzoic acid (7.5 g) in ethanol (150 ml) and the solution kept at 20° for 1 hour. On precipitation with ethanol (900 ml) the oxidised ds-RNA was separated by centrifugation, washed with ethanol (2 × 500 ml) and dissolved in 0.15 M NaCl (15 ml) to give a solution of N-oxidised ds-RNA (15.9 mg/ml).

A $\frac{280 \text{ nm}}{260 \text{ nm}}$ ratio for the product was 0.60 compared with 0.45 for ds-RNA.

To a solution of this ds-RNA N-oxide (63.6 mg) in 0.15 M NaCl (4 ml) was added dropwise with constant stirring a solution of compound 10 (22.3 mg) a 0.15 M NaCl (2.36 ml) (equivalent to 80% neutralisation). A small amount of precipitation occurred. The precipitate was removed by centrifugation and discarded. The supernatant indicated a nucleic acid complex concentration of 9.3 mg/ml. As for the parent N-oxidised ds-RNA on electrophoresis this polyquaternary ammonium complex did not move into the gel.

The antiviral activity and toxicity of this complex, Complex C13, are recorded in Table 9.

To a solution of the formaldehyde modified ds-RNA (96 mg) above in 0.15M NaCl (10 ml) a solution of compound 10 (42.1 mg) in 0.15M NaCl (2 ml) (equivalent to 100% neutralisation) was added dropwise with constant agitation.

The complex, Complex C14, had a mobility of 0.33 relative to ds-RNA and 0.44 relative to formaldehyde modified ds-RNA.

Complex C15 was prepared from the same formaldehyde modified ds-RNA but using compound 3 (377 mg) in 0.15M NaCl (equivalent to 86% neutralisation). Some precipitate formed which was removed by centrifugation. The supernatant contained the complex C15 (6 mg/ml), with a electrophoretic mobility of 0.48 relative to ds-RNA and 0.66 relative to formaldehyde modified ds-RNA.

The antiviral activities and toxicities of complexes C14 and C15 and listed in Table 9.

Table 9

Antiviral Activity and Toxicity of Ds-RNA and Soluble Modified Ds-RNA-Polyquaternary Ammonium Complexes C13, C14 & C15
No. dead out of 10 in each group

| Expt. | COMPOUND | ANTIVIRAL DATA (EMC) | | | | | | | | | | | TOXICITY (i.p.) | | | | |
|---|---|---|---|---|---|---|---|---|---|---|---|---|---|---|---|---|---|
| | | Compound administered 3 days prior to virus infection | | | | | | Compound administered 1 day prior to virus infection | | | | | | | | | |
| | | Virus Dose $10^{-4}$ | | | Virus Dose $10^{-5}$ | | | Virus Dose $10^{-4}$ | | | Virus Dose $10^{-5}$ | | | | | | |
| | | Compound Dose (mg/kg) | | | | | | | | | | | | | | | | $LD_{50}$ |
| | | 5 | 0.5 | 0.05 | 5 | 0.5 | 0.05 | 5 | 0.5 | 0.05 | 5 | 0.5 | 0.05 | 100 | 50 | 25 | 12.5 | (mg/kg) |
| | ds-RNA | 10 | 9 | 10 | 5 | 9 | 6 | 0 | 4 | 8 | 0 | 0 | 3 | | 10 | 3 | 2 | ≈30 |
| 1 | ds-RNA/N-oxide | 9 | 10 | 9 | 8 | 8 | 8 | 9 | 9 | 10 | 0 | 5 | 4 | 0 | 0 | 0 | | >100 |
| | Complex C13 | 9 | 10 | 10 | 7 | 8 | 9 | 8 | 10 | 10 | 0 | 4 | 5 | 0 | 0 | 0 | | >100[a] |
| | ds-RNA | 9 | 10 | 10 | 3 | 5 | 8 | 1 | 5 | 9 | 1 | 1 | 3 | | | | | |
| 2 | ds-RNA/CH$_{20}$ | 10 | 9 | 10 | 2 | 2 | 6 | 7 | 9 | 10 | 0 | 2 | 6 | 1[b] | 2 | 0 | | ≈100 |
| | Complex C14 | 10 | 9 | 9 | 6 | 10 | 6 | 7 | 10 | 10 | 0 | 1 | 6 | 8 | 8 | 8 | | <25 |
| | Complex C15 | 10 | 10 | 10 | 9 | 10 | 7 | 5 | 8 | 9 | 2 | 3 | 5 | 10 | 10 | 4 | | <28 |

[a]5 mice per group for toxicity test
[b]6 mice only in the group

Undosed Controls Mortality
{ Virus dose $10^{-4}$
  Expt. 1 19/20
  Expt. 2 19/20

Virus Dose $10^{-5}$
17/20
19/20

EXAMPLE 7

Preparation of an isotonic saline soluble complex from formaldehyde modified ds-RNA derived from P chrysogenum virus particles Formaldehyde modified ds-RNA was prepared as follows:

Potassium acetate (0.5 g) was added to a solution of ds-RNA (500 mg) in 0.15M saline (25 ml) to give a 0.2M acetate solution pH 8.6. Formaldehyde solution (13 ml, ca. 100 fold excess) was added and the pH adjusted from 6.7 to 8.0 with dilute sodium hydroxide. The reaction solution was incubated at 60°C for 0.5 hr., cooled to room temperature, dialysed vs 0.15M saline (3 × 5.51., pH 7.5) to yield a final solution containing ca. 10 mg/ml modified ds-RNA.

The following physical characteristics were measured:

| Tm (1/10 SSC.) | 86°C (89°C for ds-RNA) |
| Melting Range | 78–94°C (84–92°C) |
| H$_c$ | 37% (41%) |
| PAGE | 3 peaks similar to ds-RNA but with lower mobility (75%) and less distinct. |
| PAGE (in formamide) | Mobility 55% of ds-RNA |

EXAMPLE 8

Preparation of the isotonic saline soluble complexes from the low molecular weight ds-RNA derived from P. chrysogenum The low molecular weight ds-RNA (104.5 mg) isolated from P. chrysogenum (R.A. Cox, K. Kanagalingam and E.S. Sutherland, Biochem. J. 1970, 120, 549., and Biochem. J., 1971, 125, 655.) in 0.15M NaCl (5 ml) was treated with compound 10 (45.8 mg) in 0.15M NaCl (5.45 ml) for 100% neutralisation as described in Example 4 to yield Complex C16.

N.B. In the preceding examples, wherever a reference to ds-RNA from P. chrysogenum occurs, it is to be taken as meaning the high molecular weight fraction described by Cox et. al. in the above reference.

Similarly on treatment with polyquaternary ammonium compound 3, (41.0 mg) in 0.15 M NaCl (4.36 ml) for 80% neutralisation, the low molecular weight ds-RNA from P. chrysogenum formed the soluble derivative, Compound C17.

Relative to the low molecular weight ds-RNA complexes C16 and C17 had mobilities of 0.55.

The antiviral activities and toxicities are recorded in Table 10.

The material had properties similar to those outlined in Example 2 for the P. chrysogenum ds-RNA/hex- Table 10

Antiviral Activity of Ds-RNA. Low Molecular Weight, ds-RNA (from *P. chrysogenum*) and Low Molecular Weight ds-RNA - Polyquaternary Ammonium Complexes C16 and C17

No. dead out of 10 in each group

| COMPOUND | ANTIVIRAL DATA (EMC) | | | | | | | | | | | | TOXICITY (i.p.) | | | |
|---|---|---|---|---|---|---|---|---|---|---|---|---|---|---|---|---|
| | Compound administered 3 days prior to virus infection | | | | | | Compound administered 1 day prior to virus infection | | | | | | | | | |
| | Virus Dose $10^{-3}$ | | | Virus Dose $10^{-4}$ | | | Virus Dose $10^{-3}$ | | | Virus Dose $10^{-4}$ | | | | | | $LD_{50}$ |
| | \multicolumn{12}{c}{Compound Dose (mg/kg)} | | | | | |
| | 5 | 0.5 | 0.05 | 5 | 0.5 | 0.05 | 5 | 0.5 | 0.05 | 5 | 0.5 | 0.05 | 100 | 50 | 25 | 12.5 | (mg/kg) |
| Rs-RNA | 6 | 10 | 10 | 1 | 5 | 8 | 6 | 4 | 7 | 0 | 2 | 4 | | 7 | 1 | 0 | 44 |
| Low. Mol. Wt. ds-RNA | 9 | 9 | 10 | 4 | 8 | 10 | 6 | 9 | 9 | 3 | 4 | 6 | 10 | 10 | 5 | | 25 |
| Complex C16 | 9 | 10 | 10 | 8 | 9 | 9 | 5 | 6 | 10 | 0 | 1 | 5 | 9 | 10 | 7 | | 19 |
| Complex C17 | 9 | 9 | 10 | 3 | 10 | 8 | 4 | 6 | 8 | 1 | 0 | 1 | 10 | 9 | 7 | | 15 |

Undosed Controls Mortality     Viral dose $10^{-3}$ 19/20     Viral dose $10^{-4}$ 19/20

EXAMPLE 9 a. Preparation of the isotonic saline soluble complexes from the ds-RNA isolated from P. stoloniferum virus-like particles.

The ds-RNA (4 ml at 20 mg/ml) isolated from *P. stoloniferum* VLPs (W. J. Kleinschmidt et al., *Nature*, 1968, 220, 167 and G. T. Banks et al., *Nature*, 1968, 218, 542) in 0.15 ml NaCl was mixed dropwise with compound 10 (33.8 mg in 2.7 ml 0.15 M NaCl) by the usual procedure. After the addition of 2.2 ml of this solution, no more was added as there were signs of precipitation. The Complex C18 so formed thus contained 85% neutralisation.

Similarly Complex C19 was prepared from *P. stoloniferum* ds-RNA and compound 3. 66% neutralisation occurred.

| Complex | Electrophoretic Mobility Relative to *P. stoloniferum* Ds-RNA* |
|---|---|
| *P. stoloniferum* Ds-RNA | 1 and 1 |
| Complex C18 | 0.8 and 0.83 |
| Complex C19 | 0.78 and 0.78 |

*Two major peaks are obtained for *P. stoloniferum* ds-RNA, the relative mobility for the slower moving peak is given first.

b. Preparation of an isotonic saline insoluble complex from the ds-RNA isolated from P. stoloniferum virus-like particles and Hexadimethrine Bromide

*P. stoloniferum* ds-RNA (4 ml at 20 mg/ml) in 0.15M NaCl was diluted to 160 ml with 0.15 m NaCl and a solution of hexadimethrine bromide (160 mg) in 0.15 M sodium chloride (160 ml) was added at room temperature. A precipitate formed. After 18 hrs. stirring at room temperature, the precipitate was collected by centrifugation, washed with water and methanol, and finally dissolved in 1.5 M NaCl.

adimetrine bromide complex. The complex was designated $C_e$.

EXAMPLE 10

Preparation of an isotonic saline soluble and insoluble complex from the Replicative Intermediate of the sus-3 mutant of $f_2$ Coliphage To a solution of this RNA (100 mg) in 0.15 M NaCl (5 ml) was added with constant agitation a solution of compound 10 (43.8 mg) in 0.15 M NaCl (5 ml). No obvious precipitation occurred on addition, but on completion a flocculent precipitate settled which was separated by centrifugation. The supernanant (RNA concentration 5 mg/ml) was designated Complex C20. The residue was dissolved in 0.75 M NaCl (5 ml) to give an RNA concentration of 9.2 mg/ml. This is Complex Cf.

The electrophoretic mobility of complex C20 was 0.55 of the parent RNA.

The antiviral and toxicity data are given in Table 11.

EXAMPLE 11

Degradation by Pancreatic Ribonuclease

The rate of degradation of various soluble complexes by pancreatic ribonuclease was compared with that of ds-RNA and the various parent nucleic acids as indicated in Tables 12 and 13.

Ribonuclease (10 μl of a 1 mg/ml solution) in 0.15 M sodium chloride was added to a solution 100 μg of the nucleic acid or its soluble complex in 0.15 M sodium chloride solution (2.5 ml), pH 7–7.5. The optical density at 260 mm was then determined at various time intervals.

All complexes show increased resistance to pancreatic ribonuclease.

Table 11

Antiviral Activity and Toxicity of Ds-RNA. Mutant Phage Ds-RNA. and Soluble and Insoluble Mutant Phage Ds-RNA-Polyquaternary Ammonium Complexes C20 and Cf No. dead out of 10 in each group

| COMPOUND | ANTIVIRAL ACTIVITY (EMC) | | | | | | | | | | | | TOXICITY (i.p.) | | | | |
|---|---|---|---|---|---|---|---|---|---|---|---|---|---|---|---|---|---|
| | Compound administered 3 days prior to virus infection | | | | | | Compound administered 1 day prior to virus infection | | | | | | | | | | |
| | Virus Dose $10^{-4}$ | | | Virus Dose $10^{-5}$ | | | Virus Dose $10^{-4}$ | | | Virus Dose $10^{-5}$ | | | | | | | |
| | Compound Dose (mg/kg) | | | | | | | | | | | | | | | | $LD_{50}$ |
| | 5 | 0.5 | 0.05 | 5 | 0.5 | 0.05 | 5 | 0.5 | 0.05 | 5 | 0.5 | 0.05 | 100 | 50 | 25 | 12.5 | (mg/kg) |
| ds-RNA | 7 | 10 | 10 | 2 | 3 | 8 | 3 | 3 | 10 | 0 | 0 | 2 | | 7 | 1 | 0 | 44 |
| Mutant Phage ds-RNA | 10 | 9 | 10 | 8 | 9 | 6 | 10 | 9 | 2 | 3 | 3 | 3 | 10 | 10 | 9 | | < 10 |
| Complex C20 | 8 | 9 | 10 | 7 | 9 | 7 | 8 | 10 | 8 | 4 | 4 | 2 | 10 | 10 | 6 | | 22.5 |
| Complex Cf | 8 | 9 | 10 | 6 | 10 | 10 | 5 | 9 | 10 | 0 | 3 | 4 | 10 | 9 | 10 | | < 10 |

| | Undosed Controls | Viral dose $10^{-4}$ | Viral dose $10^{-5}$ |
|---|---|---|---|
| | Mortality | 20/20 | 20/20 |

Table 12

Ribonuclease Sensitivity of Ds-RNA and Complexes C3 and C10

| Expt. No. | Compound | Hc% | | | | | |
|---|---|---|---|---|---|---|---|
| | | Times after addition of ribonuclease | | | | | |
| | | 15 min. | 30 min. | 1 hr. | 2 hr. | 5 hr. | 18 hr. |
| 1 | ds-RNA | 8.6 | 16.1 | 25.8 | 37.6 | 46.2 | 46.2 |
| | Complex C3 | 0 | 0 | 0 | 0 | 0 | 0 |
| | Complex C10 | 0 | 0 | 0 | 0 | 0 | 0 |

Table 13

Ribonuclease Sensitivity of Ds-RNAs and their Polyquaternary Ammonium Complexes

| Expt. No. | Compound | Hc% | | | | | | | | |
|---|---|---|---|---|---|---|---|---|---|---|
| | | Time after addition of ribonuclease | | | | | | | | |
| | | 5 min | 10 min | 20 min | 30 min | 1 hr | 2 hr | 4 hr | 6 hr | 18 hr |
| 2 | ds-RNA | 2.2 | 4.3 | 6.5 | 10.9 | 21.7 | 35.9 | 47.8 | 48.9 | 48.9 |
| | Complex C12 | 0 | 0 | 0 | 0 | 0 | 0 | 0 | 0 | 0 |
| | ds-RNA N-oxide | 13.1 | 15.9 | 20.5 | 22.7 | 29.5 | 34.1 | 37.5 | 38.6 | 40.9 |
| | Complex C13 | 6.6 | 1.3 | 2.5 | 2.5 | 3.8 | 6.3 | 8.8 | 10.0 | 15.0 |
| | ds-RNA | 0.6 | 1.8 | 2.2 | 4.4 | 11.1 | 25.6 | 41.1 | 46.7 | 46.7 |
| 3 | ds-RNA/$CH_2O$ | 9.3 | 14.0 | 19.3 | 23.3 | 27.9 | 33.7 | 38.4 | 39.5 | 39.5 |
| | Complex C14 | 0 | 0 | 0 | 0 | 1.3 | 1.3 | 2.6 | 5.0 | 7.5 |
| | Complex C15 | 0 | 0 | 0 | 0 | 1.3 | 1.3 | 2.6 | 3.8 | 5.6 |
| | ds-RNA | 4.1 | 5.5 | 8.3 | 12.5 | 19.4 | 30.5 | 45.8 | 51.4 | 54.0 |
| 4 | Low M.W. ds-RNA | 6.3 | 13.8 | 18.8 | 25.0 | 30.0 | 37.5 | 46.3 | 47.5 | 47.5 |
| | Complex C16 | 0 | 1.5 | 1.5 | 4.6 | 4.6 | 4.6 | 6.1 | 6.1 | 12.3 |
| | Complex C17 | 0 | 0 | 0 | 1.4 | 1.4 | 1.4 | 1.4 | 1.4 | 1.4 |
| | ds-RNA | 0 | 0 | 0 | 1.2 | 6.8* | 19.3 | 35.2 | 42.0 | 46.6 |
| 5 | P. stoloniferum ds-RNA | 6.9 | 8.3 | 11.1 | 13.9 | 21.1* | 30.5 | 38.8 | 41.6 | 43.1 |
| | Complex C18 | 0 | 0 | 1.1 | 1.1 | 1.1* | 2.2 | 2.2 | 2.2 | 2.2 |
| | Complex C19 | 0 | 1.2 | 2.3 | 3.5 | 3.5* | 3.5 | 3.5 | 3.5 | 4.7 |
| | ds-RNA | 2.4 | 4.2 | 8.4 | 12.0 | 21.6 | 39.4 | 43.4 | 44.6 | 48.2 |
| 6 | Mutant Phage ds-RNA | 7.7 | 9.0 | 12.8 | 15.4 | 23.1 | 33.3 | 41.0 | 43.6 | 46.1 |
| | Complex C20 | 0 | 0 | 0 | 1.2 | 1.2 | 1.2 | 2.5 | 3.7 | 5.0 |

*Hc% at 55 min.

EXAMPLE 12

Serum Interferon Levels

The serum interferon levels for a number of complexes are given in Table 14.

Groups of 6 mice were dosed by the intraperitoneal route at 10 μg compound (in terms of RNA)/mouse. Blood was collected by cardiac puncture and pooled. The interferon levels were assayed by measurement of the reduction in the number of viral plagues, in L-929 (mouse fibroblast) cells challenged with EMC virus, caused by pretreatment of the cells with dilutions of sera. The $PDD_{50}$/ml serum is the reciprocal of the serum dilution which reduces the number of plagues to 5.0% of the control.

The soluble complexes show longer duration of high serum interferon levels.

EXAMPLE 13

Antitumour Activity

Mice, strain DBA2/J, at least eight Week old, were used and the L5178Y tumour passed weekly in an ascitic form, $10^6$ cells being injected into the peritoneal cavity. About $10^6$ tumour cells in 0.1 ml PBS were administered on the shaved flank, and the animals dosed at 8, 11, and 13 days after. The number of regressions observed per number of animals in a group are recorded in Table 15

Table 14

Serum Interferon Levels of Various Complexes
Serum Interferon $PDD_{50}$/ml serum

| | Time after administration of compound (hr.) | | | | |
|---|---|---|---|---|---|
| | 2 hr. | 4 hr. | 24 hr. | 30 hr. | 48 hr. |
| ds-RNA | 330 | 445 | 25 | 0 | 0 |
| Complex C* | 26 | 12 | | <10 | 0 |
| Complex C3 | 100 | 110 | 274 | 110 | 3 |
| Complex C10 | 59 | 260 | 64 | 56 | <10 |

*Complex C is the ds-RNA-Hexadimethrine Bromide insoluble complex.

Table 15

Tumour Regression by Ds-RNA and Complex C3

| Compound and Dose Level (μg) | Day of Dosing | Regression after Day 8 | Day 11 | Day 13 |
|---|---|---|---|---|
| ds-RNA at 10 | 8, 11, 13 | 1/6 | 3/6 | 3/6 |
| 50 | 8 | 3/6 | 4/6 | 4/6 |
| 50 | 0/6 | 0/6 | 3/6 | |
| 100 | 8 | 3/6 | 6/6 | 6/6 |
| 100 | 8, 11, 13 | 5/6 | 6/6 | 6/6 |
| Complex C3 at 10 | 8, 11, 13 | 6/6 | 6/6 | 6/6 |
| 50 | 8 | 6/6 | 6/6 | 6/6 |
| 50 | 8, 11, 13 | 6/6 | 6/6 | 6/6 |
| 100 | 8 | 6/6 | 6/6 | 6/6 |
| 100 | 8, 11 | 6/6 | 6/6 | 6/6 |
| Controls | 8, 11, 13 | 0/6 | 0/6 | 0/6 |

I claim:

1. A pharmaceutical composition useful for treating viral infections caused by any one or more of a wide variety of DNA and RNA viruses in suseptible mammals which comprises an effective serum-interferon producing ribonuclease-stable amount of an antiviral complex which is a principally ionic complex soluble in 0.15 M aqueous sodium chloride solution in which the cations are organic polymer polycations having a plurality of quaternary nitrogen sites located at intervals along the polymer chains, said polycations having the formula

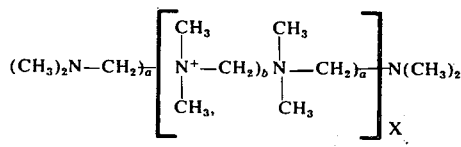

wherein each of $a$ and $b$, independent of the other, is an integer of from 2 to 6 and X is a number which is such that the average molecular weight of the polycation divided by the equivalent weight which is the molecular weight of the polycation divided by the value $(2X + 2)$ is not greater than 98, and the anions are one of: (a) double-stranded ribonucleic acid polyanions, said double-stranded ribonucleic acid being of natural origin, or (b) polyanions of a double-stranded ribonucleic acid of natural origin which has been subject to chemical or enzymatic reaction which alters one or more of the primary, secondary, and tertiary structure, provided that the resultant ribonucleic acid retains a substantial degree of base pairing between complementary strands, said antiviral complex having more than 60% of the anionic sites on the double-stranded ribonucleic acid anions neutralized by the quaternary cationic sites on the quaternary polymer, in combination with a pharmaceutically acceptable nontoxic liquid injectable or topical carrier.

2. A pharmaceutical composition according to claim 1 wherein more than 75% of the anionic sites on the double-stranded ribonucleic acid anions are neutralized by the quaternary cationic sites on the quaternary polymer.

3. A pharmaceutical composition according to claim 1 wherein the double-stranded ribonucleic acid component is from the virus particles found in infected strains of *Penicillium chrysogenum*, *Penicillium stoloniferum*, *Penicillium funiculosum*, *Penicillium cyaneofulvum*, *Aspergillus niger* or *Aspergillus foetidus*.

4. A pharmaceutical composition according to claim 1 in injectable administration form.

5. A pharmaceutical composition according to claim 1 in a form suitable for application to the mucous membrane of a susceptible mammal.

* * * * *